US00PP32313P2

(12) United States Plant Patent
Hurd

(10) Patent No.: US PP32,313 P2
(45) Date of Patent: Oct. 13, 2020

(54) ***OLEANDER* PLANT NAMED 'ATXNOKHP'**

(50) Latin Name: *Nerium oleander*
Varietal Denomination: ATXNOKHP

(71) Applicant: Kevin A. Hurd, Austin, TX (US)

(72) Inventor: Kevin A. Hurd, Austin, TX (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,659

(22) Filed: Nov. 18, 2019

(51) Int. Cl.
*A01H 5/02* (2018.01)
*A01H 6/08* (2018.01)

(52) U.S. Cl.
USPC ..... Plt./233

(58) Field of Classification Search
USPC ..... Plt./233
CPC ..... A01H 5/02; A01H 5/00; A01H 6/08
See application file for complete search history.

*Primary Examiner* — June Hwu
(74) *Attorney, Agent, or Firm* — C. A. Whealy

(57) ABSTRACT

A new and distinct cultivar of *Oleander* plant named 'ATXNOKHP', characterized by its relatively compact, upright to somewhat outwardly spreading plant habit; freely branching habit; dark green-colored leaves; freely flowering habit; dark red purple-colored flowers; and good garden performance.

2 Drawing Sheets

Figure 1:
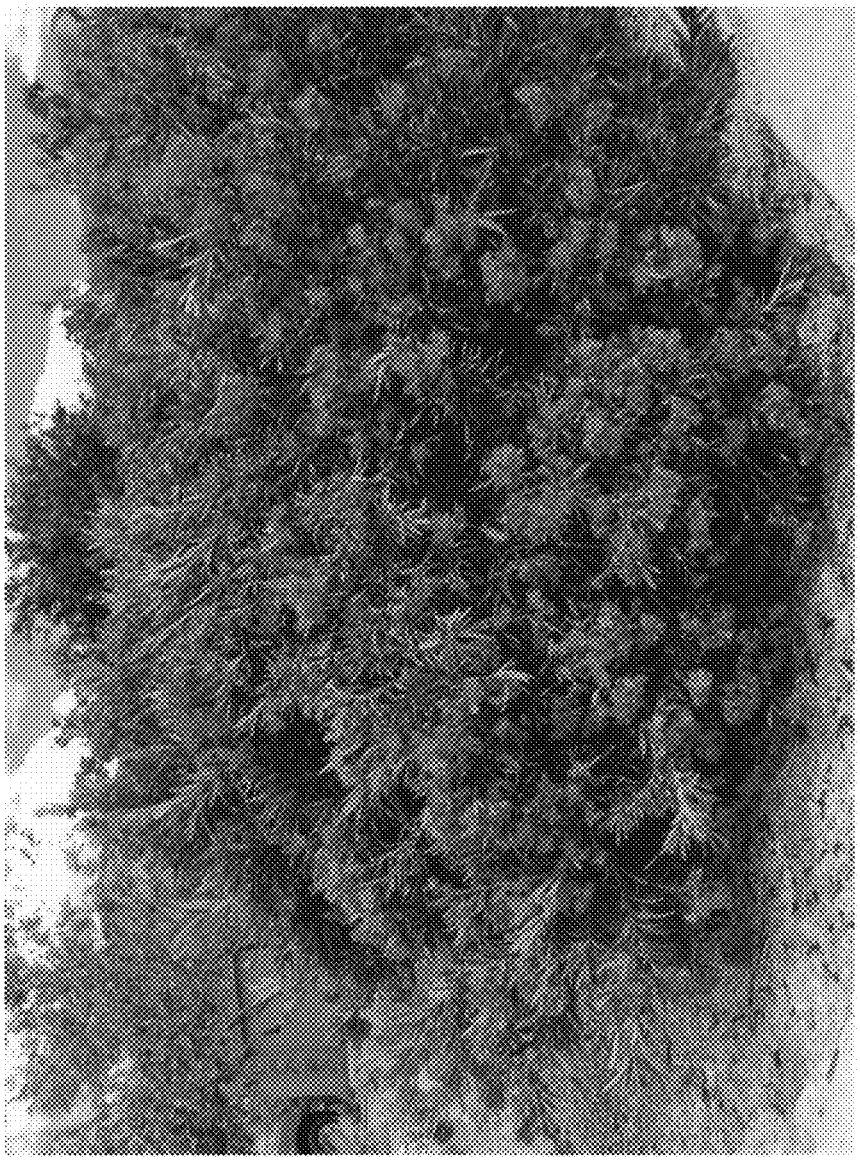

Botanical designation: *Nerium oleander.*
Cultivar denomination: 'ATXNOKHP'.

BACKGROUND OF THE INVENTION

The present invention relates to a new and distinct cultivar of *Oleander* plant, botanically known as *Nerium oleander* and hereinafter referred to by the name 'AUCNOKHP'.

The new *Oleander* plant is a product of a planned breeding program conducted by the Inventor in Austin, Tex. The objective of the breeding program is to create new compact *Oleander* plants with uniform plant habit, freely branching habit and numerous attractive flowers.

The new *Oleander* plant originated from an open-pollination in 2010 in Austin, Tex. of an unnamed selection of *Nerium oleander*, not patented, as the female, or seed, parent with an unknown selection of *Nerium oleander* as the male, or pollen, parent. The new *Oleander* plant was discovered and selected by the Inventor as a single flowering plant from within the progeny of the stated open-pollination in a controlled outdoor nursery in Austin, Tex. in May, 2014.

Asexual reproduction ofthe new *Oleander* plant by softwood stem cuttings propagated in a controlled greenhouse environment in Grand Haven, Mich. since May, 2014 has shown that the unique features of this new *Oleander* plant are stable and reproduced true to type in successive generations of asexual reproduction.

SUMMARY OF THE INVENTION

Plants of the new *Oleander* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ATXNOKHP'. These characteristics in combination distinguish 'ATXNOKHP' as a new and distinct *Oleander* plant:

1. Relatively compact, upright to somewhat outwardly spreading plant habit.
2. Freely branching habit.
3. Dark green-colored leaves.
4. Freely flowering habit.
5. Dark red purple-colored flowers.
6. Good garden performance.

Plants of the new *Oleander* differ from plants of the female parent selection in the following characteristics:

1. Plants of the new *Oleander* are more freely branching than plants of the female parent selection.
2. Flowers of plants of the new *Oleander* are darker red purple in color than flowers of plants of the female parent selection.

Plants of the new *Oleander* can be compared to plants of *Nerium oleander* 'Hardy Red', not patented. In side-by-side comparisons, plants of the new *Oleander* differ from plants of 'Hardy Red' in the following characteristics:

1. Plants of the new *Oleander* are more compact than plants of 'Hardy Red'.
2. Plants of the new *Oleander* have dark red purple-colored flowers whereas plants of 'Hardy Red' have red-colored flowers.

BRIEF DESCRIPTION OF THE PHOTOGRAPHS

The accompanying photographs illustrate the overall appearance of the new *Oleander* plant showing the colors as true as it is reasonably possible to obtain in colored reproductions of this type. Colors in the photographs may differ slightly from the color values cited in the detailed botanical description which accurately describe the colors of the new *Oleander* plant.

The photograph on the first sheet (FIG. 1 of 2) comprises a side perspective view of a typical flowering plant of 'ATXNOKHP' grown in an outdoor nursery in Austin, Tex.; the plant used in the photograph was four years old.

Figure 2:
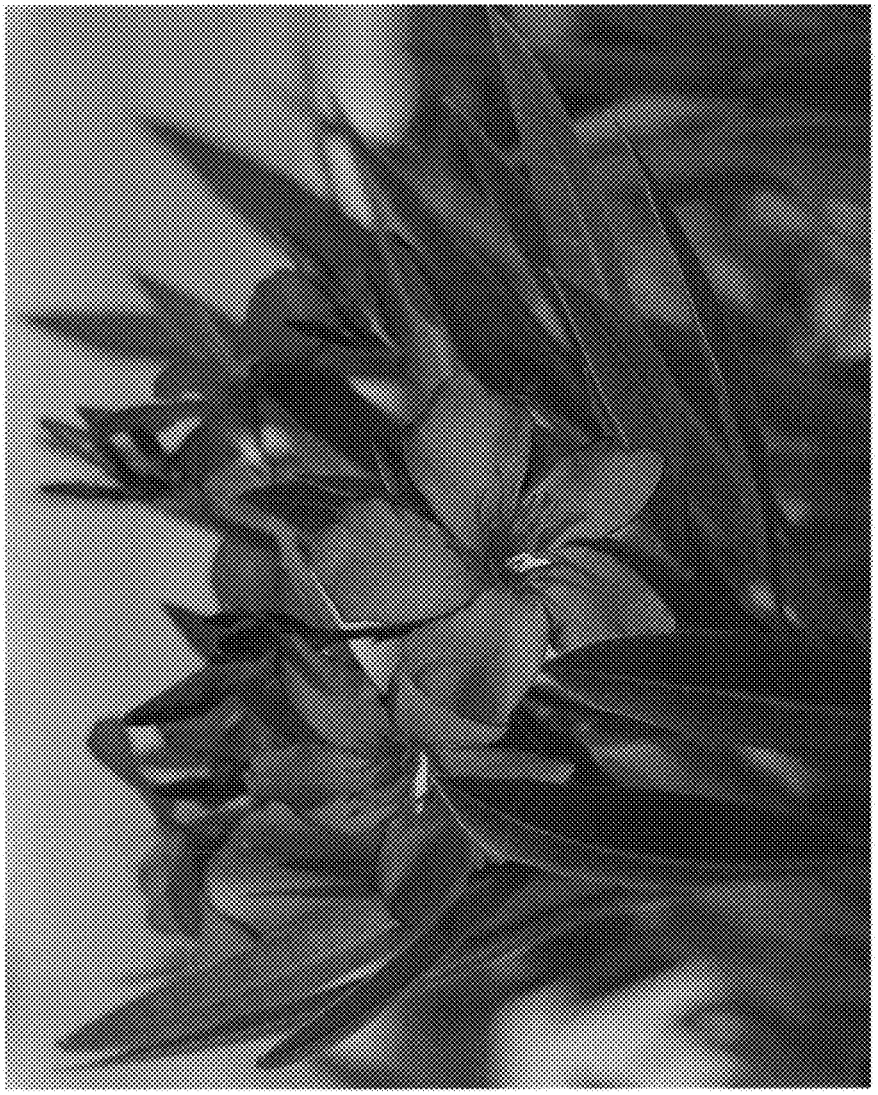

The photograph on the second sheet (FIG. 2 of 2) is a close-up view of typical flowers of 'ATXNOKHP' of a plant grown in a polyethylene-covered greenhouse environment in Grand Haven, Mich.; the plant used in the photograph was two years old.

DETAILED BOTANICAL DESCRIPTION

Plants used for the following observations and measurements were grown during the summer in three-gallon containers in a polyethylene-covered greenhouse in Grand Haven, Mich. Plants were grown under cultural practices typical of commercial Juniper plant production. During the production of the plants, day temperatures ranged from 18° C. to 27° C. and night temperatures ranged from 5° C. to 10° C. Plants were two years old when the description was taken. In the following description, color references are made to The Royal Horticultural Society Colour Chart, 2015 Edition, except where general terms of ordinary dictionary significance are used.

Botanical classification: *Nerium oleander* 'ATXNOKHP'.

Parentage:

*Female, or seed, parent.*—Unnamed selection of *Nerium oleander*, not patented.

*Male, or pollen, parent.*—Unknown selection of *Nerium oleander*, not patented.

Propagation:

*Type.*—By softwood stem cuttings.

*Time to initiate roots, summer.*—About three weeks at temperatures about 25° C.

*Time to produce a rooted young plant, summer.*—About two months at temperatures about 25° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Perennial shrub; relatively compact, upright to somewhat outwardly spreading plant habit; moderately vigorous growth habit and moderate growth rate.

*Branching habit.*—About ten basal branches develop per plant.

*Plant height.*—About 72 cm.

*Plant diameter or spread.*—About 104 cm.

*Lateral branches.*—Length: About 63 cm. Diameter: About 5 mm. Internode length: About 4 cm to 5 cm. Strength: Strong. Aspect: About 15° to 45° from vertical. Texture: Slightly pubescent. Color, developing: Close to 144C, distally, tinged with 184C. Color, developed: Close to 199B.

Leaf description:

*Arrangement.*—Whorled, simple.

*Length.*—About 12.5 cm.

*Width.*—About 1.7 cm.

*Shape.*—Narrowly elliptic to lanceolate.

*Apex.*—Acute.

*Base.*—Cuneate.

*Margin.*—Entire.

*Texture, upper and lower surfaces.*—Smooth, glabrous; leathery.

*Venation pattern.*—Pinnate.

*Color.*—Developing and fully expanded leaves, upper surface: Close to 137B; venation, close to 145C. Developing and fully expanded leaves, lower surface: Close to 147B; venation, close to 150D.

*Petioles.*—Length: About 5 mm. Diameter: About 3 mm. Texture, upper surface: Smooth, glabrous. Texture, lower surface: Slightly pubescent. Color, upper surface: Close to 145C. Color, lower surface: Close to 150D.

Flower description:

*Flower form and flowering habit.*—Single flowers arranged in terminal panicles; freely flowering habit with typically about 25 flowers developing per inflorescence; flowers face mostly upright to outwardly.

*Fragrance.*—None detected.

*Natural flowering season.*—Flowering is continuous during July and August in Michigan.

*Inflorescence height.*—About 10.5 cm.

*Inflorescence diameter.*—About 13.5 cm.

*Flower diameter.*—About 4.25 cm, throat diameter is relatively medium.

*Flower depth.*—About 4.5 cm, tube length is relatively short.

*Flower buds.*—Length: About 2.5 cm. Diameter: About 6 mm. Shape: Elliptic. Color: Proximally, close to 60B and distally, close to 60A.

*Petals.*—Quantity and arrangement: About five petals arranged in a single whorl fused towards the base. Length: About 2 cm. Width: About 1.8 cm. Shape: Obovate. Apex: Obtuse. Margin: Entire. Texture, upper and lower surfaces: Smooth, glabrous; soft. Color: When opening and fully opened, upper surface: Close to 60B, throat, close to 60B. When opening and fully opened, lower surface: Close to 186B, tube, close to 186B.

*Petaloids.*—Quantity and arrangement: About 20 fringe-like petaloids arranged in several whorls at the center of the flower and fused towards the base. Length: About 1 cm. Width: About 1 mm. Shape: Irregular, typically linear. Apex: Acute. Margin: Entire. Aspect: Semi-erect to erect. Texture, upper and lower surfaces: Smooth, glabrous; soft. Color: When opening and fully opened, upper surface: Close to 60B. When opening and fully opened, lower surface: Close to 60B.

*Sepals.*—Quantity and arrangement: Five in a single whorl; fused towards the base, moderately reflexed. Length: About 5 mm. Width: About 2 mm. Shape: Lanceolate. Apex: Acute. Margin: Entire. Texture, upper and lower surfaces: Pubescent. Color: When opening and fully opened, upper surface: Close to 187B. When opening and fully opened, lower surface: Close to 187B.

*Peduncles.*—Length: About 2 cm to 4.5 cm. Diameter: About 2 mm. Strength: Strong. Aspect: About 45° from vertical. Texture: Pubescent. Color: Close to 144C slightly tinged with close to 184C.

*Pedicels.*—Length: About 3 mm. Diameter: About 1.5 mm. Strength: Strong. Aspect: About 45° from peduncle axis. Texture: Pubescent. Color: Close to 144C slightly tinged with close to 184C.

*Reproductive organs.*—Stamens: Quantity: About five per flower, relatively strongly extruded. Filament length: About 1.5 cm. Filament color: Close to 157D. Anther length: About 1 cm. Anther shape: Lanceolate, twisting. Anther color: Close to 157D. Pollen: Moderate. Pollen color: Close to 157D. Pistils: Quantity: One per flower. Pistil length: About 1 cm. Stigma diameter: About 1 mm. Stigma color: Close to 186D. Style length: About 5 mm. Style color: Close to 186D.

*Fruits and seeds.*—To date, fruit and seed development has not been observed on plants of the new *Oleander.*

Pathogen & pest resistance: Plants of the new *Oleander* have not been observed to be resistant to pathogens and pests common to *Oleander* plants.

Temperature tolerance: Plants of the new *Oleander* have been observed to tolerate high temperatures about 45° C. and to be hardy to USDA Hardiness Zone 9.

It is claimed:

1. A new and distinct *Oleander* plant named 'ATX-NOKHP' as illustrated and described.

* * * * *